(12) United States Patent
Wagener et al.

(10) Patent No.: US 10,299,472 B2
(45) Date of Patent: *May 28, 2019

(54) COATING MATERIAL

(71) Applicants: BIO-GATE AG, Nürnberg (DE); FRAUNHOFER-GESELLSCHAFT ZUR FÖRDERUNG DER ANGEWANDTEN FORSCHUNG E.V., Munich (DE)

(72) Inventors: Michael Wagener, Bremen (DE); Klaus Dieter Vissing, Morsum (DE); Dirk Salz, Bremen (DE); Peter Steinrücke, Erlangen (DE)

(73) Assignees: BIO-GATE AG, Nurnberg (DE); FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 0 days.

This patent is subject to a terminal disclaimer.

(21) Appl. No.: 15/460,880

(22) Filed: Mar. 16, 2017

(65) Prior Publication Data

US 2017/0181428 A1 Jun. 29, 2017

Related U.S. Application Data

(62) Division of application No. 10/580,300, filed as application No. PCT/EP2004/013030 on Nov. 17, 2004, now Pat. No. 9,622,471.

(30) Foreign Application Priority Data

Nov. 17, 2003 (DE) .................................. 103 53 756

(51) Int. Cl.
| | |
|---|---|
| A01N 25/08 | (2006.01) |
| A01N 25/00 | (2006.01) |
| A01N 25/34 | (2006.01) |
| A01N 59/16 | (2006.01) |
| A01N 59/20 | (2006.01) |
| A61L 27/30 | (2006.01) |
| A61L 29/10 | (2006.01) |
| A61L 31/08 | (2006.01) |
| A01N 25/10 | (2006.01) |
| A61L 15/18 | (2006.01) |
| A61L 15/26 | (2006.01) |
| A61L 15/44 | (2006.01) |
| A61L 27/34 | (2006.01) |
| A61L 27/54 | (2006.01) |
| A61L 29/08 | (2006.01) |
| A61L 29/16 | (2006.01) |
| A61L 31/10 | (2006.01) |
| A61L 31/16 | (2006.01) |

(52) U.S. Cl.
CPC ............. *A01N 25/34* (2013.01); *A01N 25/10* (2013.01); *A01N 59/16* (2013.01); *A01N 59/20* (2013.01); *A61L 15/18* (2013.01); *A61L 15/26* (2013.01); *A61L 15/44* (2013.01); *A61L 27/306* (2013.01); *A61L 27/34* (2013.01); *A61L 27/54* (2013.01); *A61L 29/085* (2013.01); *A61L 29/106* (2013.01); *A61L 29/16* (2013.01); *A61L 31/088* (2013.01); *A61L 31/10* (2013.01); *A61L 31/16* (2013.01); *A61L 2300/102* (2013.01); *A61L 2300/104* (2013.01); *A61L 2300/404* (2013.01); *A61L 2420/02* (2013.01); *A61L 2420/08* (2013.01)

(58) Field of Classification Search
CPC ................................ A01N 25/34; A01N 59/16
See application file for complete search history.

(56) References Cited

U.S. PATENT DOCUMENTS

| | | | |
|---|---|---|---|
| 5,019,096 | A | 5/1991 | Fox, Jr. et al. |
| 5,061,567 | A | 10/1991 | Brochot et al. |
| 5,106,596 | A | 4/1992 | Clemes |
| 5,595,750 | A | 1/1997 | Jacobson et al. |
| 5,741,544 | A | 4/1998 | Mahulikar |
| 6,150,004 | A | 11/2000 | Oikawa et al. |
| 6,333,093 | B1 | 12/2001 | Burrell et al. |
| 6,486,413 | B1 | 11/2002 | Ogure |
| 7,157,145 | B2 | 1/2007 | Vissing et al. |
| 7,820,284 | B2 | 10/2010 | Terry |
| 2003/0118664 | A1 | 6/2003 | Trogolo |

FOREIGN PATENT DOCUMENTS

| | | |
|---|---|---|
| DE | 4344306 | 6/1994 |
| EP | 0328421 | 8/1989 |
| EP | 0332739 | 9/1989 |
| EP | 0360720 | 3/1990 |
| EP | 0570944 | 11/1993 |
| JP | 6-65012 | 3/1994 |
| WO | 1985/002422 | 6/1985 |
| WO | 1995/013704 | 5/1995 |
| WO | 2003/024494 | 3/2003 |
| WO | 2005/049699 | 6/2005 |

*Primary Examiner* — Kyle A Purdy
(74) *Attorney, Agent, or Firm* — Duane Morris LLP; J. Rodman Steele, Jr.; Gregory M. Lefkowitz

(57) ABSTRACT

The invention relates to an antimicrobial and preferably non-cytotoxic coating material and to use of said coating material.

20 Claims, 1 Drawing Sheet

COATING MATERIAL

Figure 1:
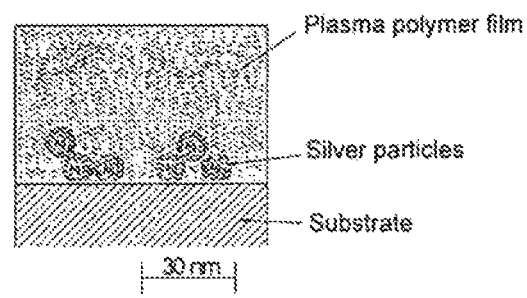

This Application is a Divisional Application of U.S. application Ser. No. 10/580,300, filed Oct. 23, 2008, which is a U.S. National Phase Application of International Application PCT/EP2004/013030, filed Nov. 17, 2004, which claims priority to German Patent Application No. 103 53 756.2, filed on Nov. 17, 2003, the entire contents of which are incorporated herein by reference.

The invention relates to an antimicrobial and preferably non-cytotoxic coating material and to use of said coating material.

In many fields, there is a persistent need to control the settlement, reproduction and survival of microorganisms, in particular of prokaryontae and fungi. There is a frequent desire, in particular, to limit the concentration of microorganisms on a certain area, or to keep said area completely free of microorganisms—or of a specific type or species of microorganism in certain cases. This aim is striven for in the medical, medical technological and sanitary-technological fields, in the broadest sense. Antimicrobial materials and coatings, such as silver-coated threads for surgery (see S. Silver, FEMS Microbiology Reviews (2003): pp. 341-353) or anti-fouling paints containing copper, are conventionally used to this end in the field of medical and sanitary products, for example. Broad-spectrum biocides, and inorganic biocides such as silver and its ions, in particular, have proved to be especially effective in this regard. In the course of time, the material treated with the biocide releases the biocide contained within it, and reduces or completely prevents the settlement or reproduction of microorganisms on the material itself, or indeed in its surroundings.

One problem in many cases is that conventional antimicrobial materials initially release a high concentration of biocide, with the consequence that the concentration of the released biocide has a toxic effect not only on the microorganisms being combated, but unintentionally on higher cells as well. This is disruptive in the case of medical products, in particular, such as wound coverings, catheters, contact lenses and implants, because a medical product treated in this way can then delay healing and result in allergies and irritation of tissue. Corresponding disadvantages also arise when biocides are released by sanitary products such as sanitary towels, tampons and diapers, and in the production and processing of foods, especially in the case of biocide-releasing packaging and biocide-releasing components for producing or processing foods. In addition, the antimicrobial effect is rapidly depleted due to leaching from the material containing the biocidic agent. Another disadvantage of conventional coatings is that they can often release a very high quantity of biocide, locally at least, if they are damaged by abrasion, for example, which can occur even when the coated objects are used in the intended manner.

In order to eliminate these disadvantages, WO 03/024494 proposes an antimicrobial adhesive and coating material containing metallic silver particles with a silver, sodium and potassium ion concentration of less than 5 ppm, the adhesive and coating material being a synthetically produced organic material that is generally hardened after processing. The silver particles are uniformly distributed in the adhesive and coating material. Specifically, the adhesive and coating material should be a varnish or adhesive, particularly a thermoset or thermoplastic varnish or adhesive. One disadvantage of the latter, however, is that the rate of metal ion release is difficult to control or adjust.

A surface wiper containing an antimicrobial agent is known from US 2002/0006887 A1. In order to delay release of the antimicrobial agent, the wiper has a poly(ethylene vinyl acetate) layer, wherein the antimicrobial agent calcium hypochlorite is totally or partially encapsulated in the coating. However, the quantities of agent released are far too great to exclude any cytotoxic effects. Use of a coating such as the one described in said document only makes sense for a wiper, but not in general for medical products, and especially not for implantable products.

A pipe containing an antimicrobial agent is known from WO 00/60297. However, said pipe does not include a transport control layer containing no particles of the antimicrobial agent. This means that the agent always comes into direct contact with the surface of the pipe, and can therefore be released in cytotoxic concentrations as well.

It was therefore an object of the present invention to define a coating material having antimicrobial properties that is simple and inexpensive to produce, but which should not be cytotoxic. A coating material is deemed to be antimicrobial if it inhibits the reproduction of *Staphylococcus epidermidis* for at least ten hours, measured as described in DE 197 58 598 A1. Such measurements determine whether bacteria of the aforementioned kind, for example, can produce less than 0.1% daughter cells on the surface des coating material within 18 hrs, compared to a control sample containing no biocidic agent. A coating material is also considered cytotoxic when it has a cytotoxic effect as described in the DIN-ISO 10993-5 standard. In addition, the coating material should have a antimicrobial and non-cytotoxic effect of maximum possible persistence. It should be usable as universally as possible, for example on fleece materials, films, plastics, metals and composite materials, and permit the production of thin coatings as well, in particular with thicknesses between 40 and 200 nm. The coating material should also contain a minimum amount of biocide. The surface characteristics of the coating material should be adjustable over as wide a range as possible. The coating material should also adhere very well to a substrate being coated, it should be as transparent, food-grade and resistant to hydrolysis as possible, and have adjustable barrier properties.

The invention therefore proposes a antimicrobial and non-cytotoxic coating material, comprising:
a) a biocide layer containing a biocidic agent, and
b) a transport control layer covering the biocide layer, having a thickness and porosity selected to release an antimicrobial and non-cytotoxic quantity of the active biocidic agent out of the biocide layer and through the transport control layer.

Compared to conventional antimicrobial materials, the coating material of the invention allows a high biocide concentration that would normally be cytotoxic to be provided in the coating material itself, wherein the total quantity of biocide can remain advantageously small. The biocide layer forms a depot of the biocidic agent, so to speak, in order to allow protracted release of the biocidic agent. By providing the transport control layer, the concentration of biocidic agent released from the biocide layer through the transport control layer is restricted to such an extent that the agent is no longer cytotoxic, yet still has an antimicrobial effect. The transport control layer can thus have a controlling and regulating function. Furthermore, the transport control layer can prevent any direct contact between the surroundings and the biocide layer. The durability of the coating material is enhanced as a result, because corrosive attack by body fluids or foodstuffs (particularly juices), for example, can be effectively stopped or restricted. The transport control layer can be disposed on both sides or only on one side of the biocide layer. The latter is specifically preferred whenever the coating material of the invention forms a coating on a solid body. In such a case, the solid coated with the coating material of the invention can cover the side of the biocide layer that is not covered by the transport control layer.

A biocidic agent within the meaning of the present invention is any substance that can develop an antimicrobial effect in the sense described above (a biocidic agent in the narrower sense). The category of biocidic agents also includes substances that produce the biocidic agent in the narrower sense by converting in the particular environment in which a coating material is to be used. For example, if the biocidic agent in the narrower sense is a metal ion, in particular a silver, copper and/or zinc cation, then metallic silver, copper and/or zinc as well alloys, complexes and other such substances are biocidic agents from which the aforesaid cations can be released into an appropriate environment, for example in the area of a wound. According to the invention, metallic biocides are preferred.

The person skilled in the art understands that a coating material according to the invention can also have antimicrobial effects against other microorganisms, and not or not only against *Staphylococcus epidemidis*. The antimicrobial efficacy of the coating material of the invention is measured in respect of other microorganisms in accordance with DE 197 58 598 A1 using the respective microorganism in place of *Staphylococcus epidermidis*. Particularly preferred are coating materials of the invention which, without being cytotoxic, have an antimicrobial effect against one or more of the microorganisms in the group comprising Bacillus, *Clostridium, Enterobacter, Escherichia, Pseudomonas, Salmonella, Staphylococcus, Yersinia, Candida*, and *Listeria*. The coating material according to the invention can also have an antiviral effect.

The transport control layer of the coating material according to the invention is preferably designed to have a gas permeability for oxygen ($O_2$) in the range between 100 and 1000 ($cm^3$ bar)/(day $m^2$), and preferably in the range between 600 and 700 ($cm^3$ bar)/(day $m^2$). Such transport control layers can be produced in a particularly appropriate manner using vacuum evaporation or plasma polymerisation. On the basis of the gas permeability criterion described above, the person skilled in the art can carry out the usual routine tests and identify suitable starting materials and parameters for producing a corresponding transport control layer. Particularly preferred transport control layers are defined in the rest of this description and in the examples.

By means of the vacuum-aided thin-layer method referred to above, in particular sputtering and plasma polymerisation, it is possible to adjust the adhesive properties, hydrolysis resistance and surface energy of the coating materials of the invention in an advantageously easy manner. Furthermore, transport control layers made in this way are transparent and can be applied to almost any substrate. There are no restrictions on processing temperature of any practical relevance.

In vacuum-aided thin-layer methods, in particular sputtering and plasma polymerisation, the hydrophilia of the coating material is preferably influenced by selecting the high oxygen content for the atmosphere chosen for making the coating. With an $O_2$ content of up to 95%, a 0.07 mbar operating atmosphere pressure (remainder of operating atmosphere: HMDSO), a plasma power of 2500 W and a reactor volume of 400 I, an advantageously strongly hydrophobic coating material is obtained (see examples). Hydrophilic coating materials according to the invention can preferably be obtained with an $O_2$ content of 40-95% (remainder of operating atmosphere: HMDSO); generally, the higher the selected $O_2$ content of the operating atmosphere, the more hydrophobic the coating material will be. Thus it is also possible to influence the rate of silver ion diffusion from the transport control layer in an advantageously simple manner; generally, the more hydrophilic the coating material, the higher the diffusion rate.

Alternatively or additionally, a hydrophilic coating material according to the invention can be produced using a vacuum-aided thin-layer method in which, after production of a transport control layer, the coating material is treated in a pure oxygen atmosphere at an operating atmosphere pressure of 0.02-0.04 mbar, preferably 0.06 mbar, using a plasma power of 500-2000 W, preferably 1000 W, in a 400 I-reactor.

Hydrophobic coating materials can be produced according to the invention using a vacuum-aided thin-layer method with an operating atmosphere comprising hydrogen and hexafluoroethane ($C_2F_6$), if necessary with a post-activation step. The ration of hydrogen to hexafluoroethane is between 2:1 and 4:1, preferably 3:1, with a plasma power of 400 W and a reactor volume of 400 I. The person skilled in the art can easily adapt the above figures to other plasma power ratings and other reactor volumes, if desired.

By means of the production process described in the foregoing, the surface energy of the coating material according to the invention is also influenced; in particular, the surface energy can be freely selected in a range from 10-105 mN/m. The higher the surface energy, the lower the tendency of *Staphylococcus epidermidis* and other microorganisms to adhere. By setting the surface energy in the manner according to the invention, it is possible to control the antimicrobial effect of the coating material of the invention in an advantageously simple manner. It is also possible to adjust the adhesion of gram-positive and/or gram-negative microorganisms in a controlled manner. In addition, a silicate-like structure enables a high level of biocompatibility to be achieved.

Particularly preferred are coating materials according to the invention in which the biocidic agent is an inorganic biocide. Such biocidic agents are generally inexpensive, easily obtainable and easy to process. The biocidic agent can be presented with a variety of methods; in particular, it can be applied to a surface that is to be coated with a coating material according to the invention. Vacuum evaporation, sputtering and chemical vapour deposition are particularly suitable methods for applying an inorganic biocidic agent.

In one particularly preferred embodiment of the coating material according to the invention, the biocidic agent is selected from the group comprising silver, copper and zinc, their ions and their metal complexes, or a mixture or alloy of said elements. These biocidic agents are effective against many different microorganisms and attack their metabolism in numerous ways. It is rarer for bacteria to become resistant when these biocides are used than when organic biocides with specific mechanisms of action, especially antibiotics, are used.

It has been found that a particularly advantageous coating material according to the invention is one in which the biocidic agent is silver, a silver cation, or a complex or alloy which releases silver or silver cations. Metallic silver, in particular, can be easily processed and is available in high quality at a relatively low price, with the result that the coating material according to the invention can be produced relatively inexpensively.

It is expedient if the biocidic agent is present in granular form in the coating material according to the invention, the primary particles preferably having a mean particle size of 5-100 nm. Biocidic agents in such fine powdery form can be easily produced, particularly for inorganic biocides and for silver in particular, but also for copper and zinc, as well as mixtures, complexes and alloys of said three metals. The biocidic agent has a high specific surface due to the mean particle size being so small, so it can be released well by diffusion from the biocide layer. Another advantageous aspect is that chemical activation of the granular agent, as sometimes required in the wound surroundings, usually affects only part of the surface due to its high specific surface, thus enabling release of the biocidic agent from the biocide layer even under adverse conditions. Coating materials of the invention in which the mean particle size of the biocidic agent is 5-50 nm, preferably 5-20 nm, have been found to be especially advantageous. When the biocidic agent is silver or a silver alloy, these particle size distributions are also referred to as nanoscale silver or nanoscale silver alloys.

Depending on the specific use, the biocide layer can have a thickness of at least 1 nm, and preferably not more than 1 mm. When using granular biocidic agents, the biocide layer is at least as thick as the granular agent. The thickness of the biocide layer is preferably 5 nm to 100 nm, layer thicknesses of 10 nm to 50 nm being particularly preferred, in particular when the biocidic agent is silver, copper and/or zinc or their ions, metal complexes or a mixture or alloy of said elements. It has been found that, in a coating material according to the invention, even such thin layers of a biocidic agent (in particular of a biocidic agent containing nanoscale silver) are sufficient to achieve a persistent antimicrobial and non-cytotoxic effect.

The biocide layer is preferably not applied over the entire surface of the substrate coated with the coating material, but instead covers only a portion of said substrate. In a locally limited area, the transport control layer is then in direct contact with the substrate and therefore adheres particularly well to the substrate. This enhanced adhesion of the transport control layer also improves the adhesion of a granular biocidic agent such as silver particles, for example, and particularly of nanoscale silver.

Vacuum-aided methods are very suitable for producing the coating material according to the invention, particularly when it is necessary to make very thin layers. In such cases it is especially preferred that the biocide layer be produced using a sputtering or evaporation deposition process, because they enable metallic biocides to be deposited directly onto the substrate, without any chemical process occurring. When the method is an impregnation or sol-gel method, in contrast, a metal salt is used that is reduced to a metal in or on the substrate. It is precisely this reduction process that frequently does not run to completion, thus making production difficult to reproduce. The production of conventional coatings, in particular by means of sol-gel methods, also gives rise to residues that must then be washed off and disposed of at some expense. Such residues can be avoided by using coating materials according to the invention that are made by vacuum-aided thin-layer methods.

Also preferred is a coating material according to the invention in which the biocidic layer also includes: gold, platinum, palladium, iridium, tin, antimony, their ions, their metal complexes, or a mixture or alloy of the biocidic substance with one or a plurality of said elements. Adding the aforesaid elements to the biocidic agent increases and/or prolongs its antimicrobial efficacy. The aforesaid element are preferably bonded in cationic form in ion exchangers, in the form of a complex or a salt, preferably of a polymeric carboxylic acid.

Also preferred is a coating material according to the invention wherein the transport control layer has a substrate material that is selected from the group comprising
a) an organic substrate material, in particular a plasma polymer, a sol-gel, a varnish or lacquer, and a siliconised substrate material, or
b) an inorganic substrate material, in particular $SiO_2$ and SiC, a metal oxide, in particular $TiO_2$ and $Al_2O_3$, and a non-biocidic metal, in particular titanium or medical stainless steel.

It is understood that the substrate material has a thickness and porosity that enable the biocidic agent to be released through the transport control layer in a concentration at which the biocidic agent thus released can act antimicrobially and non-cytotoxically. It is particularly preferred that the substrate material be microporous. It is preferred, especially when making thin layers, to produce the transport control layer using a plasma polymerisation process or sputtering. It is possible in this way to produce very thin transport control layers through which the biocidic agents, such as atomic or cationic silver, for example, can diffuse and confer on the coating material its antimicrobial, non-cytotoxic activity.

The transport control layer is preferably produced in such a way that its layer thickness, density, moisture uptake capacity, diffusion tightness against water vapour, its chemical composition and its cross-linkage structure enable the biocidic agent to be released through the transport control layer, such that the biocidic agent thus released can have antimicrobial and non-cytotoxic effects. If a sputtered or plasma polymer layer serves as the transport control layer, for example, this layer preferably has strong cross-linkings and a high diffusion tightness against water vapour and other gases or vapours, as well as a low moisture absorption capacity. A transport control layer of this kind requires only a very small layer thickness to ensure that the biocidic agent still has sufficient antimicrobial effectiveness but no cytotoxic effects.

The transport control layer is preferably selected so that bacterial adhesion is minimised. This can be achieved by adjusting the surface energy according to the type of bacteria being investigated, for example. The surface energy is adjusted by changing the layer deposition parameters as described in Example 7. The bacterial adhesion is measured quantitatively using the method described in DE 197 51 581 C2, with which the layer characteristics relating to biocompatibility (particularly non-cytotoxic properties) can be optimised while minimising the concentration of biocide.

The transport control layer according to the invention therefore allows both the cytotoxicity and the surface layer characteristics such as bacterial adhesion and the adhesion of biomolecules and cells of a preselected tissue type to be supported or suppressed in a controlled manner.

A particularly preferred coating material according to the invention is one in which the transport control layer has a silicon content of 20-60%, preferably 20-33%, a carbon content of up to 50%, in particular between 10 and 30%, and an oxygen content of 25-66%, also and specifically between 30 and 50%. It is understood here that the respective concentrations must be matched to each other in such a way that they do not exceed 100% in total. The concentrations are measured using X-ray photoelectron spectroscopy (XPS); when determining the silicon, carbon and oxygen content, elements are ignored that cannot be measured using XPS analysis, such as hydrogen, for example. Thus, in addition to silicon, carbon and oxygen, there may be other elements present in the transport control layer (namely elements that cannot be detected with XPS), without these additional elements being taken into consideration when determining the silicon, carbon and oxygen content. The silicon, carbon and oxygen content is expressed as atomic or molar percentages of the total element content detected with XPS analysis.

The transport control layer of a coating material according to the invention preferably has a mean thickness of 5 nm to 500 nm. When using a plasma polymer transport control layer, however, it is preferred that the transport control layer has a thickness of 5-200 nm, particularly a thickness not exceeding 100 nm, and preferably a thickness of 10-100 nm. With layer thicknesses of this order, and especially with transport control layers made by plasma polymerisation, it is possible to produce outstanding antimicrobial yet non-cytotoxic coating materials. These transport control layers are also very thin, so they are visually inconspicuous and may even be transparent.

It is particularly preferred that the coating material of the invention is given a transport control layer that can be produced by sputtering or plasma polymerisation. When produced in this way, it is possible to achieve very good coatings, even of bodies with complex shapes; fine-cell bodies, in particular fleece materials, can be reliably coated with a transport control layer that allows them to retain their flexibility, permeability and breatheability. Sputtering and plasma polymerisation also enable substrates to be coated that can only be coated with thick-film methods if considerable disadvantages are accepted; such substrates include bone nails and other bone implants. When said substrates are coated with conventional means, what can happen is that the coating is pushed off when the substrate is subjected to further processing, in particular during implantation in a bone, with the result that a bulge is formed locally; in such a case, the release rate of the biocidic agent is no longer uniform and controllable over the entire substrate member. In particular, the biocidic agent could be released in a cytotoxic concentration, thus delaying or preventing healing. By means of plasma polymerisation, it is also possible using the coating material of the invention to produce gradient layers for transport control, the surface characteristics of which (hydrophilic, hydrophobic, anti-adherent and transparent—further details are provided below) can preselectedly vary from one location to the next. During sputtering or plasma polymerisation, the formation of layers can be carried out ellipsometrically during deposition, for example, in order to ensure the reproducibility of the layer structure. The same type of control can also be implemented during deposition of the biocide using a sputtering or evaporation deposition process.

Thin-layer coating materials according to the invention (preferably with thicknesses up to 100 nm, see above) are also preferred. These coating materials have advantageous sealing properties, thus enabling them to be used as coatings for packaging food and medical products.

It is particularly advantageous when the biocide layer and the transport control layer both have the same substrate material. When this is the case, it is possible in particular to provide firstly a biocidic agent (in particular silver, copper and/or zinc) in preferably nanoscale form and then, by applying the substrate material of the transport control layer in a single further step, to produce the coating material of the invention and in doing so to embed the biocidic agent in said coating material.

The substrate material of the transport control layer can also be selected so that the transport control layer has additional and advantageous properties in addition to its enabling the biocidic agent to be released through the transport control layer. In particular, by selecting a suitable substrate material or by means of other measures, the transport control layer can be made transparent, hydrophilic, hydrophobic, oleophobic and/or non-adhering (also for bacteria). Particularly preferred are hydrophilic transport control layers for the medical products described in greater detail below, such as wound coverings. Medical products coated with the coating material of the invention are especially suitable for wet treatment of wounds and for improved bone growth, in particular because they guard against infections, without local tissue being damaged by excessive release of the antimicrobial agent, or its rate of healing being stopped or retarded. On the other hand, coating materials of the invention having a more hydrophobic transport control layer are particularly preferred embodiment wherever it is important for a surface to be easily wiped or cleaned, and particularly where food is processed.

The biocide layer and the coating material of the invention, in its entirety, can be present in any form. In particular, the biocide layer and the coating material of the invention can form a coating on a solid body, for example on a fibre or on a metal, plastic and/or glass surface. However, the biocide layer and the coating material of the invention can also form a coating on particles.

When silver (in particular nanoscale silver) is used as the biocidic agent, the silver content of the coating material of the invention is preferably 1-100 ppm. It has been found, surprisingly, that solid silver in a coating material according to the invention can develop a sufficiently antimicrobial effectiveness even in the quantities cited.

According to the invention, the coating material described in the foregoing, including its embodiments, can be used to produce an antimicrobial and non-cytotoxic coating on a solid body. In particular, it can be used to produce an antimicrobial and non-cytotoxic coating on a medical product, in particular a catheter, a wound covering, a contact lens, an implant, a medical nail and/or screw, bone fixation nails, a medical instrument, or on a sanitary product, in particular on a sanitary towel, a tampon or a diaper, or on packaging for a medical or sanitary product, or on a component for producing or processing foodstuffs, or on some other product requiring special hygiene precautions. As described at the beginning, there is a need in the field of medical and sanitary products, especially, for products that are antimicrobial yet non-cytotoxic. By providing conventional products with a coating material according to the invention—for example by coating them with said coating material—this need can be met in a very simple manner. The antimicrobial, non-cytotoxic coating with a adjustable surface energy is also and especially suitable for coating dental implants, wherein the osteointegration of the implant can be improved and adjusted in an advantageously simple manner by varying the surface energy.

The invention shall now be described in greater detail with reference to preferred embodiments. The Figures show in:

FIG. 1: A cross-section of an antimicrobial an non-cytotoxic coating material, FIG. 2: Plots of bacterial growth on various polyurethane surfaces.

EXAMPLE 1: MANUFACTURING A COATING MATERIAL OF THE INVENTION

A solid substrate to be coated with an antimicrobial and non-cytotoxic coating material of the invention is coated in a first coating step with a layer of porous nanoscale silver. This is achieved by vaporising metallic silver in an inert gas atmosphere, for example of argon, at an operating pressure of approximately 10 mbar. A silver coating (biocide layer) is produced on the substrate, said coating comprising single silver particles or chains of silver particles. The silver particles have a mean particle size of between 10 and 20 nm. The thickness of the silver coating (biocide layer) is approximately 20 nm.

In a second coating step, a plasma polymer layer with hexamethyldisiloxane (HMDSO) as precursor is applied. The plasma polymerisation is performed under an operating pressure of 0.07 mbar with an operating gas comprised of 95% $O_2$ and 5% HMDSO. After 45 seconds of plasma polymerisation performed under said conditions, the silver layer is coated with a hydrophilic plasma polymer (transport control layer) with a thickness of 45 nm. The surface energy of this coating is 105 mN/m.

Medical products in particular, such as wound coverings and catheters, can be coated in this manner with a coating material according to the invention.

EXAMPLE 2: MANUFACTURING A COATING MATERIAL ACCORDING TO THE INVENTION USING AN ADHESION-PROMOTING LAYER

A substrate to be coated with a coating material of the invention is coated in a first step with a titanium dioxide film by means of plasma polymerisation. The precursor used is titanium tetraisopropyloxide in a mixture with oxygen. The polymerisation time is five minutes. A $TiO_2$ film 25 nm thick and with good adhesiveness is formed.

In a second coating step, a thin metallic silver layer is deposited on the $TiO_2$ film in an ultrahigh vacuum. During deposition, the process pressure is $10^{-4}$ mbar. Vaporisation is carried out in such a way that a silver layer (biocide layer) of 10-20 nm thickness is deposited on the $TiO_2$ film.

In a third coating step, a plasma polymer film (transport control layer) is applied to the silver layer. Plasma polymerisation is carried out as described in Example 1. A highly hydrophilic plasma polymer layer of 45 nm thickness is formed.

The following materials can be coated particularly well using the coating material according to the invention: metals, in particular titanium and (medical) stainless steel, plastics, in particular polyurethane, and cellulose, in particular wound coverings and cellulose fleece.

EXAMPLE 3: APPLYING A TRANSPORT CONTROL LAYER ONTO A BIOCIDIC SOLID

A plasma polymer film is deposited as a transport control layer on a solid layer of copper using the plasma polymerisation method described in Example 1. In contrast to Example 1, the plasma coating process is carried out for 450 seconds. The transport control layer thus produced has a thickness of 100 nm. A coating material according to the invention is obtained, the biocide layer being the original layer of solid copper.

EXAMPLE 4: ANALYSIS OF A COATING MATERIAL ACCORDING TO THE INVENTION, PRODUCED USING THE PROCESS IN EXAMPLE 1

According to XPS analysis, the surface of the transport control layer has a silicon content of 36.6%, a carbon content of 24% and an oxygen content of 39.4%. The hydrogen content cannot be measured using XPS analysis. The infrared spectrum of the coating material also shows a small amount of methyl groups. Thus, although the transport control layer is principally inorganic, it still has a small concentration of organic groups.

According to energy dispersion X-ray analysis, the ratio between the silicon and silver concentrations in the coating material of the invention is approximately 10:1. In relation to all the chemical elements (with the exception of hydrogen) that form the coating material of the invention, the silver content is less than 3% by weight.

Distribution of the silver in the coating material of the invention is not homogenous. FIG. 1 shows schematically that there is only a very small silver content in the outer 40-50 nm of the coating material facing away from the substrate. Under this outer 40-50 nm layer (transport control layer) there is a nanoscale silver-containing layer of approx. 20 nm thickness (biocide layer) that also contains, in addition to silver, the other elements of the substrate material of the transport control layer. The nanoscale silver is therefore embedded as a biocide layer in the substrate material of the transport control layer.

Figure 2:
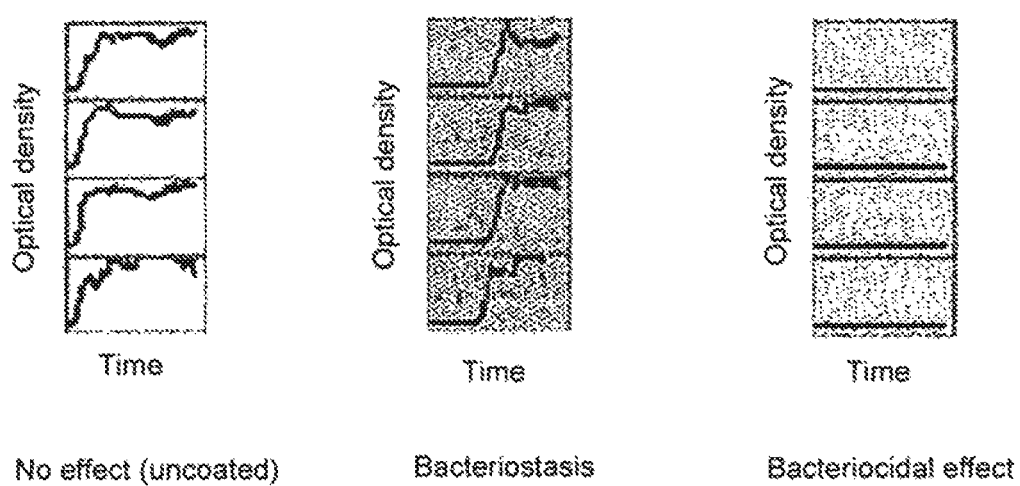

FIG. 2 shows proof of the antimicrobial effect of a polyurethane surface coated with a coating material of the invention in accordance with Example 1, compared to an untreated polyurethane surface. The antimicrobial effect was tested against *Staphylococcus epidermidis* in the manner described in DE 197 58 598 A1. FIG. 2 shows the change in optical density and hence in the bacterial count over a 24-hour period. The sub-figure on the left shows the plot of bacterial growth on an untreated polyurethane surface. The sub-figures in the middle and on the right show the plots of bacterial growth on polyurethane surfaces coated with different coating materials of the invention.

It can be seen that bacterial growth occurs on the untreated polyurethane surface within a very short time, whereas no growth in the bacterial cell counts (sub-figure on the right) occurs on the coating material of the invention within the period shown, or that significantly delayed bacterial growth occurs (sub-figure in the middle). The coating material of the invention is therefore antimicrobial. It is also non-cytotoxic within the meaning of DIN-ISO10993-5 (no Figure).

EXAMPLE 5: PROCESS FOR MANUFACTURING ANOTHER COATING MATERIAL OF THE INVENTION

A solid substrate to be coated with an antimicrobial and non-cytotoxic coating material of the invention is coated in a first coating step with a layer of porous nanoscale silver. This is achieved by vaporising metallic silver in an inert gas atmosphere, for example of argon, at an operating pressure of approximately 10 mbar. A silver coating (biocide layer) is produced on the substrate, said coating comprising single silver particles or chains of silver particles. The silver particles have a mean particle size of between 10 and 20 nm. The thickness of the silver coating (biocide layer) is approximately 20 nm.

In a second coating step, a transport control plasma polymer layer with hexamethyldisiloxane (HMDSO) as precursor is applied. The plasma polymerisation is performed in a reactor with a volume of 400 l at an operating pressure of 0.07 mbar, with a plasma power of 2500 W and with an operating gas comprised of 95% $O_2$ and 5% HMDSO. After 45 seconds of plasma polymerisation performed under said conditions, the silver layer is coated with a plasma polymer layer of 45 nm thickness. The antimicrobial effect leads to a 35-hour shift in the measured signal pursuant to DE 197 58 598 A1, so the coating material is practically self-sterilising; however, the bacterial adhesion is not reduced in comparison with the uncoated polyurethane substrate.

In a third step of the process, oxygen activation is carried out for two minutes under 1500 W of power, an oxygen flow von 100 sccm and at an operating pressure of 0.04 mbar. After oxygen activation, the surface energy increases to 105 nN/m and the bacterial adhesion is reduced to approx. 10% of the initial value.

EXAMPLE 6: PROCESS FOR MANUFACTURING ANOTHER COATING MATERIAL OF THE INVENTION

An antibacterially effective and a haemocompatible transport control layer are combined by preparing a copper-containing fluorocarbon layer. The biocide layer is applied in a DC magnetron sputtering process using a copper target. At a partial pressure of the ionisation gas, argon, of $5*10^{-2}$ mbar, a porous copper layer is formed on the substrate. In a second step of the process, the transport control layer is applied to the biocide layer by means of a plasma polymerisation process with hexafluoroethane ($C_2F_6$) as precursor. To increase the rate of deposition, hydrogen is added to the $C_2F_6$ at a ratio of 3:1. At an operating pressure of 0.1 mbar, after a process time of 3 min, a fluorocarbon layer with a film thickness of 55 nm and a surface energy of 19 mN/m is formed. In a final step, the copper of the biocide layer is oxidised in a tempering step at 50° C. in an oxygen atmosphere to form copper(I) oxide. The fluorine content in the transport control layer is 54.8%, that of carbon is 42.5% and that of oxygen is 2.7%. Half of the fluorine itself is present as $CF_2$ groups, one third as $CF_3$ and one sixth as CF groups.

EXAMPLE 7: PROCESS FOR MANUFACTURING ANOTHER COATING MATERIAL OF THE INVENTION

In Example 1, a plasma polymer film with hexamethyldisiloxane (HMDSO) as precursor is used as the transport control layer. The surface of this layer can then be modified in a third step. By depositing a very thin silicone-like film with an HMDSO precursor, the surface energy can be set within a range from 105 mN/m to 22 mN/m, without significantly affecting its anti-bacterial characteristics. With the surface modified in this way, it is possible to control the growth behaviour not only of bacteria, but also of other cells.

EXAMPLE 8: PROCESS FOR MANUFACTURING ANOTHER COATING MATERIAL OF THE INVENTION

If a vanadium target is used in non-reactive DC sputtering, it is possible to produce vanadium films of appropriate porosity to serve as biocide layers. The thickness of this layer is in the 50 nm range. To form the transport control layer, a plasma polymer film based on acrylic acid is deposited using plasma polymerisation. After half an hour of deposition with an acrylic acid flow of 40 sccm and an argon flow of 200 sccm, a film 50 nm thick is generated, the infrared spectrum of which is identical to that of polyacrylamide gel. The layers prepared in this manner have a high surface energy of approx. 55 mN/m that is also stable over long periods of time.

EXAMPLE 9

The transport control layer does not necessarily have to be produced by a plasma polymerisation process; a reactive middle-frequency (MF) sputtering process will also produce a deployable layer. The Si target is sputtered under a $8*10-4$ mbar partial pressure of the ionisation gas argon and a partial oxygen pressure of $2*10-4$ mbar. These layers are free of carbon and have an atomic composition of Si:O=1:2. In addition to surface modification of the transport control layer, it is possible by means of impregnation process to impregnate calcium ions into the layer, for example. This is done by dipping the antibacterial layer for 24 hours in a 0.01 molar solution of calcium hydroxide. In a further step of the process, a "ship-in-a-bottle" reaction, the impregnated calcium hydroxide can be converted, for example, to calcium chloride, calcium sulphate or calcium carbonate. In addition to calcium ions, it is also possible in a subsequent impregnation process to bind BMPs (bone morphogenetic proteins) to the surface of the coating. The layers modified in this way allow improved bone cell growth.

The invention claimed is:

1. A device having an antimicrobial and non-cytotoxic coating, comprising:
   a) a substrate comprising a surface, wherein:
      (i) the substrate comprises a material selected from the group consisting of metal and plastic,
      (ii) the substrate has a form selected from the group consisting of particles and fibers, or
      (iii) both option (i) and option (ii);
   b) a biocide layer covering the surface, said biocide layer having a biocidal active agent in the form of single particles, chains of particles, or both, and
   c) a transport control layer covering the biocide layer, having a thickness and porosity adjusted to release an antimicrobial and non-cytotoxic quantity of the biocidal active agent out of the biocide layer and through the transport control layer,
   wherein the transport control layer is a plasma polymer layer and/or a sputter-applied layer and wherein the transport control layer has a silicon content of 20 to 60%, a carbon content between 10 and 30% and an oxygen content of 30 to 50%, wherein the transport control layer is hydrophilic, wherein the particles of the single particles or chains of particles have a mean particle size of 5-100 nm.

2. The device of claim 1, wherein said device is selected from the group consisting of an implant, a bone fixation screw, and a dental implant.

3. The device of claim 1, wherein the substrate comprises a material selected from the group consisting of metal and plastic.

4. The device of claim 1, wherein the substrate has a form selected from the group consisting of particles and fibers.

5. The device of claim 1, wherein the transport control layer has a gas permeability for oxygen ($O_2$) which is in the range from 100 to 1000 ($cm^3$ bar)/(day $m^2$).

6. The device of claim 1, wherein the transport control layer has a gas permeability for oxygen ($O_2$) which is in the range from 500 to 700 ($cm^3$ bar)/(day $m^2$).

7. The device of claim 1, wherein the biocidal active agent is selected from the group consisting of silver, copper and zinc, their ions and their metal complexes, or a mixture or alloy comprising two or more of said elements.

8. The device of claim 7, wherein the biocide layer further comprises: gold, platinum, palladium, iridium, tin, antimony, their ions, their metal complexes, or an alloy of the biocidal active agent with one or more of said elements.

9. The device of claim 1, wherein the coating comprises a substrate material that is selected from the group consisting of
a) an organic substrate material, selected from the group consisting of a plasma polymer, a sol-gel, a coating, and a siliconised substrate material,
b) an inorganic substrate material, selected from the group consisting of $SiO_2$ and SiC, a metal oxide and a non-biocidal metal, and
c) a combination thereof.

10. The device of claim 9, wherein the metal oxide is $TiO_2$, $Al_2O_3$ or a combination thereof, and wherein the non-biocidal metal is titanium, medical stainless steel, or a combination thereof.

11. The device of claim 1, wherein the transport control layer has a mean thickness of 5-500 nm.

12. The device of claim 1, wherein said device is selected from the group consisting of a catheter, a wound covering, an implant, a medical nail, a medical screw, a bone fixation nail, a dental implant, a medical instrument, and a sanitary product.

13. The device of claim 1, wherein the biocidal active agent comprises an agent selected from the group consisting of silver, silver ions, and silver complexes.

14. A device having an antimicrobial and non-cytotoxic coating, comprising:
a) a substrate comprising a surface, wherein:
(i) the substrate comprises a material selected from the group consisting of metal and plastic,
(ii) the substrate has a form selected from the group consisting of particles and fibers, or
(iii) both option (i) and option (ii);
b) a biocide layer covering the surface, said biocide layer having a biocidal active agent in the form of single particles, chains of particles, or both, and
c) a transport control layer covering the biocide layer, having a thickness and porosity adjusted to release an antimicrobial and non-cytotoxic quantity of the biocidal active agent out of the biocide layer and through the transport control layer,
wherein the transport control layer contacts the biocide layer,
wherein the transport control layer is a plasma polymer layer and/or a sputter-applied layer and wherein the transport control layer has a silicon content of 20 to 60%, a carbon content between 10 and 30% and an oxygen content of 30 to 50%, wherein the transport control layer is hydrophilic, wherein the particles of the single particles or chains of single particles have a mean particle size of 5-100 nm.

15. The device of claim 14, wherein said device is selected from the group consisting of an implant, a bone fixation screw, and a dental implant.

16. The device of claim 14, wherein the substrate comprises a material selected from the group consisting of metal and plastic.

17. The device of claim 14, wherein the substrate has a form selected from the group consisting of particles and fibers.

18. The device of claim 14, wherein said device is selected from the group consisting of a catheter, a wound covering, an implant, a medical nail, a medical screw, a bone fixation nail, a dental implant, a medical instrument, and a sanitary product.

19. The device of claim 14, wherein the biocidal active agent comprises an agent selected from the group consisting of silver, silver ions, and silver complexes.

20. The device of claim 1, wherein the substrate comprises plastic.

* * * * *